United States Patent [19]

Green

[11] Patent Number: 4,734,525

[45] Date of Patent: Mar. 29, 1988

[54] PROCESS FOR THE PRODUCTION OF FORMATES

[75] Inventor: Michael J. Green, Hedon, England

[73] Assignee: BP Chemicals Limited

[21] Appl. No.: 533,981

[22] Filed: Sep. 20, 1983

[30] Foreign Application Priority Data

Sep. 25, 1982 [GB] United Kingdom ............ 8227416
Sep. 25, 1982 [GB] United Kingdom ............ 8227417
Oct. 7, 1982 [GB] United Kingdom ............ 8228687
Oct. 7, 1982 [GB] United Kingdom ............ 8228688

[51] Int. Cl.$^4$ .................... C07C 67/36; C07C 69/06
[52] U.S. Cl. ............................................. 560/232
[58] Field of Search ................................. 560/232

[56] References Cited

FOREIGN PATENT DOCUMENTS 1084549 9/1967 United Kingdom ............ 560/232

OTHER PUBLICATIONS

Kudo et al., Nippon Kagaku Kaishi, 1977, vol. 4, pp. 457–465.

Primary Examiner—Vivian Garner
Attorney, Agent, or Firm—Brooks Haidt Haffner & Delahunty

[57] ABSTRACT

An alkyl ester of formic acid is prepared by reacting carbon monoxide with an alcohol in the presence, as catalyst, of (a) a guanidine or (b) an amidine and an epoxide.

The amidine or guanidine structure can by cyclic. The process can be operated in the liquid phase at pressures from 20 to 120 bars and temperatures from 40° to 150° C. with excess carbon monoxide over that required for conversion of the alcohol to the formate ester.

15 Claims, No Drawings

PROCESS FOR THE PRODUCTION OF FORMATES

This invention relates to a process for the preparation of alkyl esters of formic acid by the carbonylation of alcohols. Alkyl esters of formic acid can be readily hydrolysed to formic acid itself which is a valuable chemical used for the treatment of crops and as a chemical intermediate.

It has been previously reported in Nippon Kagaku Kaishi (1977, Vol 4, pages 457–465) that methanol can be carbonylated to methyl formate using, as catalyst, 1,8-diazabicyclo[5.4.0]undec-7-ene or 1,5-diazabicyclo[4.3.0]non-5-ene which are cyclic amidines and are herein referred to as DBU and DBN respectively.

It has now been found that a catalyst which comprises a guanidine or a mixture of an amidine and an epoxide gives an improved conversion of alcohol as compared with the above mentioned published art.

Thus, according to the present invention a process for the preparation of an alkyl ester of formic acid comprises reacting carbon monoxide with an alcohol in the presence of, as catalyst, an effective amount of (a) a compound containing a guanidine group or (b) a compound containing an amidine group and a compound containing an epoxide group.

By the term amidine is meant a compound containing the grouping

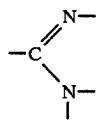

Conveniently the free valencies on the nitrogen atoms are attached to carbon atoms or hydrogen and the free valency on the carbon to another carbon atom or nitrogen atom. In the latter case the structure will be a guanidine. The term amidine in the present specification is therefore intended to include guanidine.

The amidine can be a cyclic compound as for example in 1,5-diazabicyclo [4.3.0]non-5-ene which has the formula

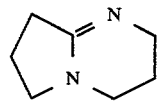

or 1,8 diazabicyclo[5.4.0]undec-7-ene of the formula

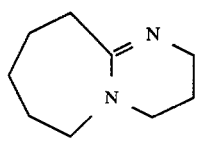

or 1,5,7 triazabicyclo[4.4.0]dec-5-ene of formula

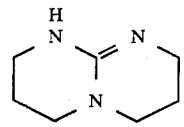

The epoxide group containing compound is conveniently a 1:2 alkylene oxide such as a lower alkylene oxide, e.g., ethylene oxide, 1:2 propylene oxide or 1:2 butylene oxide.

Preferably the molar proportion of amidine group containing compound to epoxide group containing compound is in the range 5:1 to 1:5.

The amount of catalyst (either guanidine or epoxide and amidine mixture) is preferably from 0.01 to 50% more preferably from 1 to 20% by weight based on the weight of reactants.

Conveniently the process is carried out under superatmospheric pressure, for example, in the range 20 to 120 bar and at elevated temperature, for example in the range 40° to 100° C.

The alcohol is conveniently an alkanol containing from 1 to 10 carbon atoms but may be an aralkyl alcohol, e.g., benzyl alcohol. The term alkyl in the present specification is therefore intended to include aralkyl.

Preferably the alcohol is a primary or secondary lower (e.g., $C_1$ to $C_6$) aliphatic alcohol, for example methanol, ethanol, n-propanol, or isopropanol, or n-butanol, or secondary butanol.

Conveniently carbon monoxide is continuously supplied to the reaction zone to replenish the carbon monoxide used in the reaction.

By the term guanidine group is meant the group of formula:

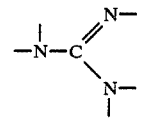

The free valencies on the nitrogen atoms can be attached to hydrogen or carbon atoms. The guanidine group can be embodied in a cyclic structure as for example in 1,5,7-triazabicyclo[4.4.0]dec-5-ene which has the formula shown above.

In the case of an acyclic guanidine it is preferred that one or more of the nitrogen atoms bear inert organic substituents selected for example from lower alkyl ($C_1$ to $C_6$) such as methyl, ethyl and propyl (which alkyl can be substituted for example by trialkoxysilyl) or monovalent organic cyclic structures such as piperidinyl.

An acyclic guandine can have five alkyl or substituted alkyl on the nitrogen atoms thereof. The alkyl groups can be $C_1$ to $C_{10}$.

The invention is illustrated by the following Examples. In all the Examples the reactants and products (except the carbon monoxide) were maintained in the liquid phase and the catalyst was employed in solution.

EXAMPLE 1

Production of methyl formate from methanol.

A 100 ml high pressure stirred autoclave was charged with 23.9 gm of methanol, 1.7 gm of 1:2 propylene oxide, and 3.6 gm of 1,5-diazabicyclo[4.3.0]non-5-ene (DBN). The autoclave was sealed and flushed twice with carbon monoxide and finally heated to 60° C. with stirring (1200 rpm). Rapid gas absorption occurred and the pressure was maintained between 48 and and 56 bar by replenishment from a cylinder. After 3 hours, gas absorption had ceased and the autoclave was cooled to 0° C. Analysis of the liquid product by gas chromatography showed a methanol conversion of 77% with a selectivity to methyl formate of 98%.

EXAMPLE 2

Production of methyl formate from methanol.

Example 1 was repeated except that 4.4 gm of 1,8-diazabicyclo [5.4.0]undec-7-ene was used in place of DBN. Analysis of the product mixture showed a methanol conversion of 46% with a selectivity to methyl formate of 95%.

EXAMPLE 3

Production of methyl formate from methanol.

Example 1 was repeated except that 4.3 gm of 1,5,7-triazabicyclo [4.4.0]dec-5-ene was used in place of DBN. Analysis of the product mixture showed a methanol conversion of 58% with a selectivity to methyl formate of 93%.

EXAMPLE 4

Production of methyl formate from methanol.

Example 1 was repeated except that 3.6 gm of N,N,N',N'-tetramethyl guanidine was used in place of DBN and the reaction was carried out at 80° C. Analysis of the product mixture showed a methanol conversion of 12% with a selectivity to methyl formate of 85%.

EXAMPLE 5

Production of methyl formate from methanol.

Example 1 was repeated except that 2.1 gm of 1:2 butene oxide was used in place of propene oxide. Analysis of the product mixture showed a methanol coversion of 83% with a selectivity to methyl formate of 99%.

EXAMPLE 6

Production of ethyl formate from ethanol.

The autoclave described in example 1 was charged with 26 gm of ethanol, 1.8 gm of 1.2 propylene oxide, and 3.9 gm of DBN. After flushing twice with carbon monoxide, the autoclave was pressurised to 83 bar with carbon monoxide and heated to 80° C. with stirring (1200 rpm). Rapid gas absorption occurred and the pressure was maintained between 75 and 85 bar by replenishment from a cylinder. After 40 min gas absorption had ceased and the autoclave was cooled to 0° C. Analysis of the product mixture showed an ethanol coversion of 67% with a selectivity to ethyl formate of 98%.

EXAMPLE 7

Production of n-propyl formate from n-propanol.

Example 6 was repeated except that 26 gm of n-propanol was used in place of ethanol. Analysis of the product mixture showed a propanol conversion of 81% with a selectivity to propyl formate of 98%.

COMPARATIVE EXPERIMENT 1

Example 1 was repeated in the absence of propylene oxide. Analysis of the product mixture showed a methanol conversion of only 2%. This experiment illustrates that DBN alone is not an effective carbonylation catalyst under the conditions of Example 1.

COMPARATIVE EXPERIMENT 2

Example 1 was repeated except that 3.2 gm of triethylamine was used in place of DBN. Analysis of the product mixture showed a methanol conversion of 26% with a selectivity to methyl formate of 93%.

This experiment compared with Example 1 illustrates that the combination of amidine and epoxide gives a far higher conversion of methanol than does the combination of triethylamine and epoxide.

EXAMPLE 8

A 100 ml high pressure stirred autoclave was charged with 25.4 gm of methanol and 4.3 gm of 1,5,7-triazabicyclo[4.4.0]dec-5-ene (TBD). The autoclave was sealed and flushed twice with carbon monoxide, following which it was pressurised to 50 bar with carbon monoxide and finally heated to 120° C. with stirring (1200 rpm). Rapid gas absorption occurred and the pressure was maintained between 48 and 56 bar by replenishment from a cylinder. After 30 min, gas absorption had ceased and the autoclave was cooled to 0° C. Analysis of the liquid product by gas chromatography showed a methanol conversion of 38%, with methyl formate being the only detectable product.

EXAMPLE 9

Example 8 was repeated except that the temperature was maintained at 80° C. for 3 hours. Analysis of the liquid product showed a methanol conversion of 36% with a total selectivity to methyl formate.

EXAMPLE 10

Example 8 was repeated except that 4.3 gm of $N,N,N^1,N^1$-tetramethyl-$N^{11}$-(3-trimethoxysillylpropyl) guanidine (TPG) was used in place of TBD and the reaction was continued for 3 hours. Analysis of the product mixture showed a methanol conversion of 25% to methyl formate.

EXAMPLE 11

Example 8 was repeated except that 3.7 gm of $N,N,N^1,N^1$-tetramethyl-$N^{1\,1}$-octanoyl guanidine was used in place of TBD and the reaction was continued for 3 hours. Analysis of the product mixture showed a methanol conversion of 7% to methyl formate.

EXAMPLE 12

Example 8 was repeated except that 3.6 gm of $N,N,N^1,N^1$-tetramethylguanidine was used as a catalyst in place of TBD and the reaction was continued for 3 hours. Analysis of the product mixture showed a methanol conversion of 13% to methyl formate.

EXAMPLE 13

Example 8 was repeated except that 5.7 gm of $N,N^{1}$-Dicyclohexyl-$N^{11}$-[2,2,6,6-tetramethyl-piperidinyl-]guanidine was used as a catalyst in place of TBD and the reaction was continued for 3 hours. Analysis of the product mixture showed a methanol conversion of 15% to methyl formate.

EXAMPLE 14

The autoclave described in Example 8 was charged with 26 gm of ethanol and 4.3 gm of TBD and sealed. After flushing twice with carbon monoxide, the autoclave was pressurised to 88 bar with carbon monoxide and heated to 120° C. for 2 hours with stirring (1200 rpm). Analysis of the product mixture showed an ethanol conversion of 37% with a total selectivity to ethyl formate.

EXAMPLE 15

The autoclave described in Example 8 was charged with 26 gm of n-propanol and 3.3 gm of TBD and sealed. After flushing twice with carbon monoxide, the autoclave was pressurised to 91 bar with carbon monoxide and heated to 120° C. for 2 hours with stirring (1200 rpm). Analysis of the product mixture showed a propanol conversion of 28% with a total selectivity to n-propyl formate.

COMPARATIVE EXPERIMENT 3

Example 14 was repeated except that 4.4 gm of 1,8-diazabicyclo [5.4.0]undec-7-ene DBU was used in place of TBD. Analysis of the product mixture showed an ethanol conversion of 5% to ethyl formate.

Comparison of this experiment with Example 14 shows a conversion of ethanol in ethyl formate using DBU was only 5% whereas it was 37% using TBD in Example 14. This demonstrates the greater activity of the TBD.

I claim:

1. A process for the preparation of an alkyl ester of formic acid which process comprises reacting carbon monoxide with an alcohol in the presence of, as catalyst, an effective amount of (a) a compound containing a guanidine group or (b) a compound containing an amidine group and a compound containing an epoxide group.

2. A process as claimed in claim 1 wherein the molar proportion of the amidine group containing compound to epoxide group containing compound is from 5:1 to 1:5.

3. A process as claimed in claim 1 wherein the guanidine group is a cyclic structure.

4. A process as claimed in claim 1 wherein the guanidine group is acyclic and at least one of the nitrogen atoms bears an inert monovalent organic substituent.

5. A process as claimed in claim 4 wherein the guanidine has alkyl or substituted alkyl substituents on the three nitrogen atoms.

6. A process as claimed in claim 1 wherein the pressure is in the range from 20 to 120 bars and the temperature from 40° to 150° C.

7. A process as claimed in claim 1, wherein the alcohol is an alkanol having from 1 to 10 carbon atoms.

8. A process as claimed in claim 1, wherein the alcohol is selected from the group consisting of benzyl alcohol, methanol, ethanol, n-propanol, isopropanol, n-butanol and secondary butanol.

9. A process as claimed in claim 1, wherein the compound of (b) containing an epoxide group is selected from the group consisting of ethylene oxide, 1:2-propylene oxide, and 1:2-butylene oxide.

10. A process as claimed in claim 1, wherein the amount of the catalyst is from 0.01 to 50% by weight based on the weight of the reactants.

11. A process as claimed in claim 1, wherein the amount of the catalyst is from 1 to 20% by weight based on the weight of the reactants.

12. A process as claimed in claim 1, wherein the catalyst is a compound of (a) containing a guanidine group which is selected from the group consisting of N,N,$N^1$,$N^1$-tetramethyl guanidine, 1,5,7-triazabicyclo[4.4.0]dec-5-ene, N,N,$N^1$,$N^1$-tetramethyl-$N^{11}$-(3-trimethoxysilylpropyl)-guanidine, N,N,$N^1$,$N^1$-tetramethyl-$N^{11}$-octanoyl-guanidine, and N,$N^1$-dicyclohexyl-$N^{11}$-(2,2,6,6-tetramethyl-piperidinyl)-guanidine.

13. A process as claimed in claim 1, wherein the compound of (b) containing an amidine group is selected from the group consisting of 1,5-diazabicyclo-[4.3.0]-non-5-ene and 1,8-diazabicyclo-[5.4.0.]-undec-7-ene.

14. A process for the preparation of an alkyl ester of formic acid which process comprises reacting carbon monoxide with an alkanol having from 1 to 10 carbon atoms in the presence of, as catalyst from 0.01 to 50% by weight based on the weight of the reactants of (a) a compound containing a guanidine group and selected from the group consisting of N,N,$N^1$,$N^1$-tetramethyl guanidine, 1,5,7-triazabicyclo[4.4.0]dec-5-ene, N,N,$N^1$,$N^1$-tetramethyl-$N^{11}$-(3-trimethoxysilylpropyl)-guanidine, N,N,$N^1$,$N^1$-tetramethyl-$N^{11}$-octanoyl-guanidine, and N,$N^1$-dicyclohexyl-$N^{11}$-(2,2,6,6-tetramethyl-piperidinyl)-guanidine, or (b) a compound containing an amidine group and selected from the group consisting of 1,5-diazabicyclo-[4.3.0]-non-5-ene and 1,8-diazabicyclo-[5.4.0]-undec-7-ene, and a compound containing an epoxide group, and selected from the group consisting of ethylene oxide, 1:2-propylene oxide, and 1:2-butylene oxide.

15. A process for the preparation of an alkyl ester of formic acid which process comprises reacting carbon monoxide with an alcohol in the presence of, as catalyst, an effective amount of a compound containing a guanidine group.

* * * * *

UNITED STATES PATENT AND TRADEMARK OFFICE
CERTIFICATE OF CORRECTION

PATENT NO. : 4,734,525
DATED : March 29, 1988
INVENTOR(S) : Michael J. Green

It is certified that error appears in the above-identified patent and that said Letters Patent is hereby corrected as shown below:

Col. 4, line 37 correct spelling of "(3-trimethoxysilylpropyl)"

Signed and Sealed this

Twenty-fifth Day of October, 1988

Attest:

DONALD J. QUIGG

Attesting Officer

Commissioner of Patents and Trademarks